Figure 1:
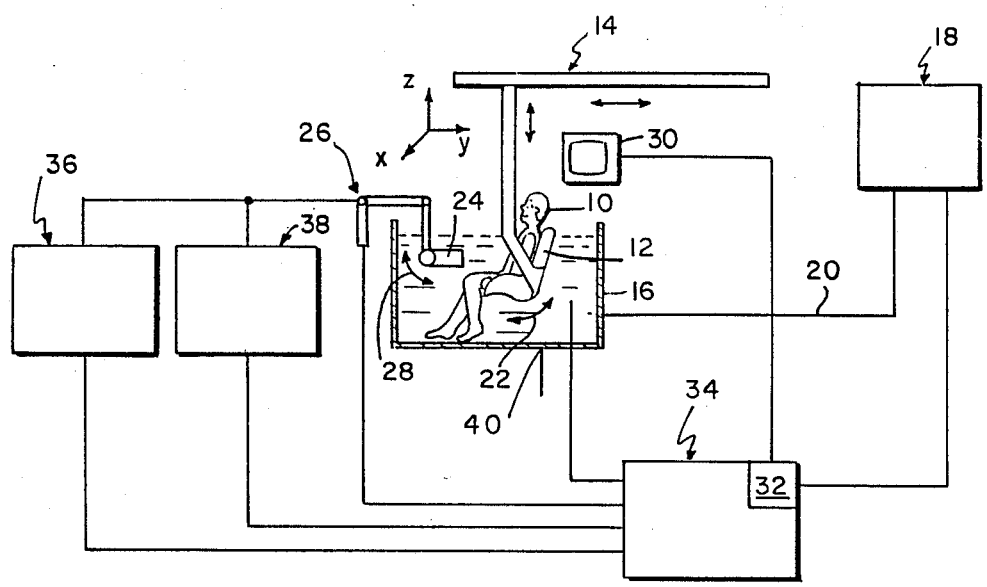

United States Patent [19]

Fry et al.

[11] Patent Number: 4,917,095
[45] Date of Patent: Apr. 17, 1990

[54] ULTRASOUND LOCATION AND THERAPY METHOD AND APPARATUS FOR CALCULI IN THE BODY

[75] Inventors: Francis J. Fry; Bryan Burney, both of Indianapolis, Ind.

[73] Assignee: Indianapolis Center for Advanced Research, Inc., Indianapolis, Ind.

[21] Appl. No.: 798,973

[22] Filed: Nov. 18, 1985

[51] Int. Cl.⁴ .............................................. A61B 10/00
[52] U.S. Cl. ............................ 128/660.03; 128/24 A
[58] Field of Search ................. 128/660, 303 R, 24 A, 128/328

[56] References Cited

U.S. PATENT DOCUMENTS

| | | | |
|---|---|---|---|
| 4,216,766 | 8/1980 | Duykers et al. | 128/24 A |
| 4,484,569 | 11/1984 | Driller et al. | 128/24 A |
| 4,526,168 | 7/1985 | Hassler et al. | 128/303 R |
| 4,556,070 | 12/1985 | Vaguine et al. | |
| 4,590,922 | 5/1986 | Gordon | 128/1.1 |
| 4,620,545 | 11/1986 | Shene et al. | |

Primary Examiner—Edward M. Coven
Attorney, Agent, or Firm—Barnes & Thornburg

[57] ABSTRACT

An apparatus and a method for non-invasively decomposing a calculus in a human body include a mechanism for, and the step of, locating the calculus, a mechanism for, and the step of, delivering to the site of the calculus a chemical species known to reduce the calculus, and a mechanism for, and the step of, generating an unfocussed beam of ultrasound radiation for insonating the calculus for enhancing the chemical dissolution of the calculus through the interaction of the calculus, the chemical species and the ultrasound radiation.

19 Claims, 1 Drawing Sheet

ULTRASOUND LOCATION AND THERAPY METHOD AND APPARATUS FOR CALCULI IN THE BODY

A system for visualization and non-invasive destruction of gallstones and other similar types of calculi within the body contains a real-time ultrasound visualization system for location and identification of the calculi from outside the body. An appropriate transducer coupled to a main visualization electronics and display (MVED) module or console performs these functions. An appropriate transducer, also coupled to the MVED, can then be used to guide an appropriate transcutaneous penetrating needle (typically 26 gauge to 20 gauge) into the vicinity of the calculus, such as the gall bladder, for subsequent infusion of chemicals to aid in the destruction process as needed. Other directed cannulae operating within internal body regions and body duct systems can also be used in the chemical infusion process, where appropriate. Then an appropriate transducer, typically a sector scanner with operating frequency 3.5 to 7.5 MHz, connected to the MVED, having a fixed position relative to the ultrasound therapy transducer and its sound beam, is used to position the ultrasound therapy beam so that it impinges on the calculus.

One configuration of the ultrasound therapy beam provides a broad beam with minimal focusing. The transducer source is of the order of 3 to 5 inches (7.62 to 12.7 cm) in diameter, and has a half-power beam width of from 1 to 2 inches (2.54 to 5.08 cm) at the focal position and position of use. The visualization and guidance transducer illustratively is coaxial and cofocal with the therapy transducer in order to provide easy and convenient guidance for the therapy beam. The broad therapeutic beam frequency is in the 100 kHz to 500 kHz range. This range provides the necessary minimal attenuation and absorption so that tissue from the skin surface through various organ surfaces within the body to the location of the calculus is not irreversibly affected when it is irradiated. The appropriate delivery format for the sound intensity needed with the broad beam system to produce appropriate (complete or near complete) erosion is typically a 5 second continuous wave pulse followed by a 10 second time-off period. This sequence is repeated for a total time necessary for complete stone erosion, typically thirty minutes to an hour. This format provides for tissue which experiences local temperature rises during irradiation to return to base temperature in the off period and limits temperature rise during the 5-second time-on period to a maximum of 3° to 4° C. Such temperature rises and cycles in the region of the gall bladder, for example, offer no hazard to the normal body tissues found there.

In order to produce full gallstone erosion with this limited temperature rise, the spatial peak-temporal peak (SPTP) intensity at the beam focus (broad beam) in a degassed water bath must be limited to 10 W/cm$^2$ to 20 W/cm$^2$ with the 10 W/cm$^2$ SPTP corresponding to the 500 kHz therapeutic frequency, and the 20 W/cm$^2$ SPTP intensity corresponding to the 100 kHz frequency. Full gallstone erosion at such intensities is achieved in a short time period (typically 10 to 30 minutes of ultrasound time-on) by combining the ultrasound with an injection of an appropriate chemical, such as monooctanoin or methyl-tert-butyl ether, into the gall bladder. Monooctanoin is presently preferred as the lipid solvent because of its otherwise innocuous nature. Frequently, after the combined chemical and ultrasound treatment, an insoluble, black-appearing component is left in the form of small particles or laminar structures. This component has recently been shown to be composed of mucin, bilirubin and bilirubin monoglucuronide. Two chemical reducing agents which are appropriate for interaction with the bilirubin-mucin complex are 2-mercaptoethanol and N-acetylcysteine. We have discovered that the chemical reaction of these chemicals with gallstones is greatly enhanced by irradiating the gallstones with ultrasound.

Because of the physical structure and composition of human gallstones, there are occasions when it is desirable to penetrate the hard outer core of some stones with a highly focussed boring beam so that the interior of the stone can be eroded more rapidly. This boring is achieved by using a broad beam transducer which drives a gallstone into close contact with the gall bladder wall and holds it against the wall by virtue of radiation pressure. Then a more highly focussed beam, typically at a 500 kHz to 1 MHz frequency, is used to bore through the outer crust. This boring is accomplished with relatively few (typically 10 to 20) bursts of ultrasound (2 to 5 seconds time-on, 10 seconds time-off) of SPTP intensity in the 20 to 100 W/cm$^2$ range. Once a hole has been formed in the outer shell, the lower intensity broad beam is used as described above. Location of the stone for boring is achieved since the boring beam and the therapy field radiation force beam are coaxial and cofocal with the diagnostic beam.

Two methods are used for providing delivery of ultrasound from the transducer(s) to the skin surface of the patient. In one method, a patient is suspended and oriented in a controlled temperature degassed water bath so that the entry region for the ultrasound beam(s) through the patient's skin is in the water bath. The patient is constrained and positioned so that the skin region overlying the approach to the gall bladder is in a near vertical to a somewhat reclining position. The patient is tilted to elevate the patient's right side somewhat with respect to the patient's left side. In this method, the thin transcutaneous needle for gall bladder injection is submerged in the degassed water, and the transducer is brought into the water bath by its transport system and is then guided to the gall bladder site by the real-time ultrasound identification and location system. Fine adjustments of the transducer to the patient gall bladder site are provided by controlled motions of the transducer, under direct ultrasound visualization control. Any slight readjustment needed during the therapy session can be manually controlled or automatically maintained through a visualization feedback loop.

In a second method, which is presently preferred, the patient is not immersed. Rather, the ultrasound is delivered through a front end attachment on the transducer system. This attachment houses temperature-controlled degassed water which transmits the sound from the transducer(s) surface(s) to a flexible diaphragm on the attachment, which contacts the patient's skin surface. The flexible diaphragm is ultrasonically coupled to the skin using degassed mineral oil or other appropriate coupling medium. The needle for injection of erosion-assisting chemicals into the gall bladder is outside the contact area of the diaphragm. Alternatively, if the treating physician uses a needle and connecting tubing of a special flexible type which can tolerate skin surface contact and overlying force without significantly moving the puncture position of the needle in the gall bladder, then the needle can be placed in the contact area of the diaphragm.

Although the direct needle puncture applied transcutaneously is presently preferred, it is also possible to place chemical species in the gall bladder exit duct system and into the gall bladder proper with a trans-esophageal endoscopic steerable catheter system under fluoroscopic and/or endoscopic visualization. The catheter can be directed into the common bile duct.

Once the gallstone is maximally eroded, there may exist one or more very small seeds (1 to 2 mm in size) of chemically different composition from cholesterol, the major component of typical gallstones. Most of these seeds can be flushed through the bile duct with fluid supplied through the indwelling needle or through a catheter in the gall bladder. Passage of the seed or seeds can be facilitated by intravenous injection of chemicals to expand and relax the gallbladder and ducts or to contract the gallbladder.

Figure 2:
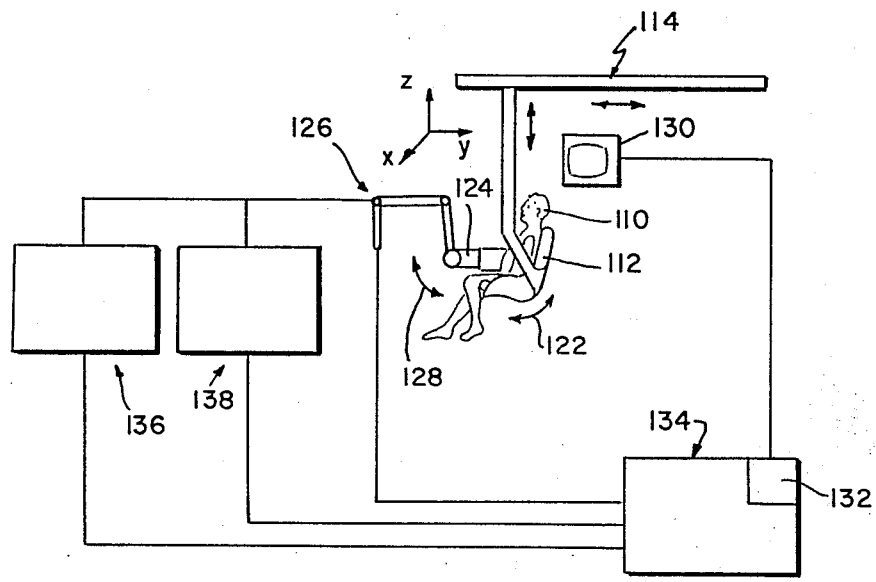

The invention may best be understood by referring to the following description and accompanying drawings which illustrate the invention. In the drawings:

FIG. 1 is a block diagram of a system constructed according to the present invention in which the patient is partially immersed in temperature-controlled degassed water; and FIG. 2 is a block diagram of a system constructed according to the present invention in which the patient is not immersed, but the transducers are immersed in a bath of temperature-controlled degassed water.

Referring now particularly to FIG. 1, a patient 10 is strapped into a chair 12 which has adjustable head, leg and arm rests. The chair 12 is also articulated between the seat and back rest and between the seat and leg rests. After appropriate pre-ultrasound irradiation procedures have been performed (gall bladder location, transcutaneous needle or trans-espheageal catheter insertion into the region of the gall bladder as required for the prescribed treatment, medication, etc.), the patient is transported by a patient transport mechanism 14 into a tank 16. Degassed water at an appropriate temperature from a degassed water supply 18 is supplied through a degassed water conduit 20 to tank 16. The tank 16 is filled to cover the body region to be irradiated for ultrasound location and therapy of the gallstones in the gall bladder or bile duct system. The chair 12 has two angular motions, one shown by curved arrow 22 and another at right angles to motion 22 so that the right side of the patient can be elevated with respect to the left side.

A transducer unit 24, having both visualization and therapy elements, is immersed in the degassed water and brought into the appropriate position. A transducer support system 26 provides five degrees of freedom for the unit 24. These include an angular motion 28 and another angular motion at right angles to angular motion 28. Additionally, x, y, and z motions of relatively small magnitude (2 to 3 inches—5.08 to 7.62 cm —total motion along each axis) permit final position adjustments, by remote or manual control, while observing the patient 10 and the gall bladder on video monitor 30 located adjacent the bath 16 or on a monitor 32 associated with a control console 34. Gross movements bring transducer unit 24 and the five degrees of freedom transducer support 26 into approximate working position with respect to the patient 10. Once the patient 10 and transducer 24 are in position, they are locked in position to prevent relative movement between patient 10 and transducer 24. Since the basic gallstone erosion process is minimally focal in nature, placement accuracy of the transducer beam center with respect to the gall bladder site selected has a tolerance in the range of 3 to 4 mm. Automatic tracking of the transducer 24 beam with respect to the gall bladder and associated stone(s) is also provided through a control loop comprising an ultrasonic visualization transducer in unit 24, associated visualization and control electronics 36, and a computer in console 34.

Most patients can be treated with a frontal approach to the gallbladder. The typical acoustic window at the skin surface for this approach is of the order of four centimeters in diameter. A fraction of patients, perhaps twenty percent, may require a lateral approach through the rib interspace. In these patients, the acoustic window at the skin surface is typically 1.5 centimeters by 6 centimeters. The long dimension of this window runs along the slightly curved rib line. This approach requires a transducer arrangement matched to this acoustic window size.

Power for a therapy transducer in unit 24 is provided by an amplifier 38. The control loop contains a power meter arrangement, not shown, to keep the power to the therapy transducer in unit 24 (and hence its power output) constant during the therapy procedure. The dosage parameters selected (power to the therapy transducer and hence its power output, time-on and time-off of the ultrasound in each delivery cycle, and total number of cycles) are under the control of the computer in console 34. Patient input information and other pertinent data are supplied through the computer in console 34.

After completion of the procedure, the water is drained through drain 40 and the patient 10 is removed from the system.

Referring now particularly to FIG. 2, a patient 110 is strapped into a chair 112 which has adjustable head, leg and arm rests. The chair 112 is articulated between the seat and back rest and between the seat and leg rests. The chair 112 has two angular motions, one shown by curved arrow 122 and another at right angles to motion 122 so that the right side of the patient can be elevated with respect to the left side. Appropriate pre-ultrasound irradiation procedures (gall bladder location, transcutaneous needle or trans-espheageal catheter insertion into the region of the gall bladder as required for the prescribed treatment, medication, etc.) are performed.

A transducer unit 124 provided with an apppropriate coupler of the general type described in, for example, U.S. Pat. No. 4,059,098, and having both visualization and therapy elements, is brought into the appropriate position. A transducer support system 126 provides five degrees of freedom for the unit 124. These include an angular motion 128 and another angular motion at right angles to angular motion 128. Additionally, x, y, and z motions of relatively small magnitude (2 to 3 inches—5.08 to 7.62 cm—total motion along each axis) permit final position adjustments, by remote or manual control, while observing the patient 110 and the gall bladder on video monitor 130 located adjacent the patient 110 location or on a monitor 132 associated with a control console 134. Gross movements bring transducer unit 124 and the five degrees of freedom transducer support 126 into approximate working position with respect to the patient 110. Once the patient 110 and transducer 124 are in position, they are locked in position to prevent relative movement between patient 110 and transducer 124. Since the basic gallstone erosion process is minimally focal in nature, placement accuracy of the transducer beam center with respect to the gall bladder site selected has a tolerance in the range of 3 to 4 mm. Automatic tracking of the transducer 124 beam with respect to the gall bladder and associated stone(s) is also provided through a control loop comprising an ultrasonic visualization transducer in unit 124, associated visualization and control electronics 136, and a computer in console 134.

Power for a therapy transducer in unit 124 is provided by an amplifier 138. The control loop contains a power meter arrangement, not shown, to keep the power to the therapy transducer in unit 124 (and hence its power output) constant during the therapy procedure. The dosage parameters selected (power to the therapy transducer and hence its power output, time-on and time-off of the ultrasound in each delivery cycle, and total number of cycles) are under the control of the computer in console 134. Patient input information and other pertinent data are supplied through the computer in console 134.

After completion of the procedure, the patient 110 is removed from the system.

What is claimed is:

1. Means for non-invasively decomposing a calculus within a human body comprising means for locating the calculus, means for ultrasonically irradiating the calculus without appreciably raising the temperature of the calculus or of the surrounding tissue, the means for locating the calculus being relatively more narrowly focussed and less powerful than the means for ultrasonically irradiating the calculus which is less narrowly focussed and more powerful than the means for locating the calculus, and means for coupling the locating means and the irradiating means for movement of the irradiating means under the control of the locating means so that location of the calculus results in appropriate aiming of the irradiating means.

2. The system of claim 1 and further comprising means for coupling the locating means and the irradiating means to the surface of the body.

3. The system of claim 2 wherein the coupling means comprises an ultrasound coupler, and means for attaching the ultrasound coupler to the locating means and to the irradiating means.

4. The apparatus of claim 2 wherein the coupling means comprises a tank, means for filling the tank with an ultrasound coupling medium, and means for suspending the body, the locating means and the irradiating means within the tank during location and irradiation of the calculus.

5. The apparatus of claim 4 wherein the means for suspending the body within the tank comprises a seat, means for immobilizing the body in the seat, and means for movably mounting the seat within the tank relative to the locating means and the irradiating means to position the body appropriately relative to the locating means and the irradiating means for location and decomposition of the calculus.

6. The apparatus of claim 1 and further comprising means for movably mounting the locating means and irradiating means to position the locating means and irradiating means appropriately relative to the body for location and decomposition of the calculus.

7. The apparatus of claim 1 and further comprising means for ultrasonically boring through the exterior of the calculus to expose its interior to the ultrasonic irradiating means, and means for coupling the boring means for movement under the control of the locating means so that location of the calculus results in appropriate aiming of the boring means.

8. The apparatus of claim 1 and further comprising means for introducing into the site of the calculus a chemical species capable of reducing the calculus, the ultrasound irradiation provided by the means for ultrasonically irradiating the calculus enhancing the rate of reduction of the calculus by the chemical species.

9. The system of claim 1 wherein the means for locating the calculus comprises means for ultrasonically locating the calculus.

10. A method for non-invasively decomposing a calculus within a human body comprising locating the calculus using a locating beam having a certain power and focus and aiming at the calculus, and exposing the calculus to, decomposing ultrasound irradiation from an irradiating transducer having a less focussed and more powerful beam than the locating beam without appreciably raising the temperature of the calculus or of the surrounding tissue.

11. The method of claim 10 and further comprising the step of substantially simultaneously locating the calculus using the locating means and aiming the irradiating transducer at the calculus.

12. The method of claim 11 and further comprising the step of coupling the locating means and the irradiating transducer to the body.

13. The method of claim 12 wherein the coupling step comprises the steps of providing an ultrasound coupler and attaching the coupler to the locating means and to the irradiating transducer.

14. The method of claim 12 wherein the coupling step comprises the steps of providing a tank, filling the tank with an ultrasound coupling medium and suspending the body within the tank during the location and irradiation of the calculus.

15. The method of claim 14 wherein the step of suspending the body within the tank during location and irradiation of the calculus comprises the steps of positioning the body on a seat, immobilizing the body with respect to the seat, and moving the seat within the tank relative to the locating means and the irradiating transducer to position the body appropriately relative to the locating means and irradiating transducer for location and decomposition of the calculus.

16. The method of claim 10 and further comprising the step of movably mounting the locating means and irradiating transducer to position the locating means and the irradiating transducer appropriately relative to the body for location and decomposition of the calculus.

17. The method of claim 10 and further comprising the steps of ultrasonically boring through the exterior of the calculus using a boring transducer to expose the interior of the calculus to the ultrasonic irradiating transducer, and coupling the boring transducer for movement under the control of the locating means so that location of the calculus results in appropriate aiming of the boring transducer.

18. The method of claim 10 and further comprising the step of introducing into the site of the calculus a chemical species capable of reducing the calculus, the step of aiming at the calculus, and exposing the calculus to, decomposing ultrasound irradiation from an irradiating transducer having a relatively less narrowly focused, relatively more powerful beam enhancing the rate of reduction of the calculus by the chemical species.

19. The method of claim 10 wherein the step of locating the calculus using a locating means comprises the step of ultrasonically locating the calculus using a locating transducer.

* * * * *